US007223328B2

United States Patent
Fleury et al.

(10) Patent No.: US 7,223,328 B2
(45) Date of Patent: *May 29, 2007

(54) SENSORS FOR REDUCING GAS MOLECULES

(75) Inventors: Vincent Fleury, Paris (FR); Thierry Devers, Chartres (FR); Lévi Allam, Chartres (FR)

(73) Assignee: Centre National de la Recherche Scientifique, Paris (FR)

( * ) Notice: Subject to any disclaimer, the term of this patent is extended or adjusted under 35 U.S.C. 154(b) by 490 days.

This patent is subject to a terminal disclaimer.

(21) Appl. No.: 10/343,205

(22) PCT Filed: Jul. 18, 2001

(86) PCT No.: PCT/FR01/02343

§ 371 (c)(1),
(2), (4) Date: Jan. 29, 2003

(87) PCT Pub. No.: WO02/10730

PCT Pub. Date: Feb. 7, 2002

(65) Prior Publication Data

US 2003/0182985 A1  Oct. 2, 2003

(30) Foreign Application Priority Data

Aug. 1, 2000 (FR) .................................. 00 10147

(51) Int. Cl.
*C25D 21/12* (2006.01)
*C25D 5/16* (2006.01)
*C25D 1/00* (2006.01)
*B32B 5/02* (2006.01)
*B32B 27/04* (2006.01)

(52) U.S. Cl. ............................ 205/84; 205/67; 205/78; 205/80; 205/82; 205/95; 205/159; 205/161; 204/450; 204/471; 422/83; 422/94; 422/95; 422/96; 422/97; 422/98; 427/58; 427/126.1; 427/126.3; 29/592.1

(58) Field of Classification Search ............... 29/592.1; 205/159, 161, 162, 67, 78, 80, 82, 84, 95; 422/83, 94, 95, 96, 97, 98; 427/58, 126.1, 427/126.3

See application file for complete search history.

(56) References Cited

U.S. PATENT DOCUMENTS 2,407,579 A      9/1946  Schweikher
5,494,701 A *    2/1996  Clough et al. ............ 427/126.3
6,764,586 B1 *   7/2004  Fleury ......................... 205/159

FOREIGN PATENT DOCUMENTS

| EP | 0 297 732 | 1/1989 |
|----|-----------|--------|
| GB | 2 321 336 | 7/1998 |
| JP | 7-103925  | 4/1995 |
| WO | WO95/00837 | 1/1995 |

OTHER PUBLICATIONS

A. S. Bakin et al., "$SnO_2$ Based Gas Sensitive Sensor", Thin Solid Films 296 (1997) pp. 168-171.

* cited by examiner

*Primary Examiner*—Brian Sines
(74) *Attorney, Agent, or Firm*—Buchanan Ingersoll & Rooney PC

(57) ABSTRACT

Provided is a gas molecule sensor, characterized in that the sensing element is a polycrystalline tin oxide film having a thickness less than 1 μm. The sensing element is produced by electrolytic deposit of a tin film on an insulating support in an electromechanical cell, where the anode is comprised of tin and the cathode is a conductive film applied on the surface of the insulating support at one of its ends, the two electrodes being separated by an electrolyte comprised of a tin salt solution, and by passing a constant current through said cell. The deposit step is followed by an oxidizing step.

9 Claims, No Drawings

SENSORS FOR REDUCING GAS MOLECULES

BACKGROUND OF THE INVENTION

1. Field of the Invention

The invention relates to a sensor for reducing gas molecules, the sensitive element of which is tin oxide.

2. Description of the Related Art

The detection and measurement of the concentration of harmful molecules in an atmosphere constitutes a very major challenge, especially because of the increase in emissions of industrial or municipal origin. It has become necessary to detect the presence of harmful molecules in ever decreasing concentrations, below the concentrations of danger to humans. The case of carbon monoxide CO, found in particular in exhaust gases and in cigarette smoke, is one example, this gas being fatal at extremely low concentrations, of the order of 1 ppm. Furthermore, these same molecules must be detected in certain industrial or technological devices such as fuel cells, in which very low concentrations cause, for example, catalysts to be poisoned. The sensitivity threshold and the speed of detection are the two important parameters of a sensor of this type.

It is known to use tin oxide sensors to detect reducing gas molecules. The conductivity of tin oxide, which is an intrinsic semiconductor, varies according to the content of reducing molecules in the atmosphere. It is accepted that, in a nonreducing atmosphere, oxygen is adsorbed at the grain boundaries and partially repels the grain boundary electronic states, making the material highly resistive. In the presence of reducing molecules, the oxygen concentration at the grain boundaries decreases, thus releasing the electronic states near the surface of the grains, on either side of the actual contact surface. The existence of these electronic states allows conduction of electrons across the grain boundaries. It is thus apparent that the sensitivity of the sensors having tin oxide as sensitive element increases when the oxide grain size decreases, that is to say when the specific surface area increases and when the quantum effect of repelling the electronic states toward the interior of the grain is more effective. However, reducing the grain size in general causes a reduction in the physical connectivity between the grains, to the detriment of the conductivity.

Such sensors whose sensitive element is a tin oxide are described, for example in the special issue "*Gas-sensing Materials*" of Materials Research Society Bulletin, published in June 1998. They comprise a polycrystalline tin oxide layer on a support. In commercialized devices, tin oxide grain size is in general of the order of 1 μm. Also known are sensors containing polycrystalline tin oxide as active material in the form of grains having a size of less than 20 nm. These are essentially laboratory devices, produced by preparing the oxide from a metal obtained by sputtering, by laser ablation, by sol-gel processes, by precipitation or by other chemical synthesis processes. When the oxide is obtained by a sol-gel process or by simple precipitation, it contains a solvent that has to be removed. In most cases, the oxide obtained is in the form of a powder of separate grains, which then has to be sintered and fired so that it can be used for a sensor, and the physical connectivity of the grains is not guaranteed. Furthermore, sintering results in a three-dimensional material in the form of wafers that contain a large number of grains through the thickness. The response time of a sensor containing such an oxide will be longer the thicker the wafers, because of the time needed for the gas molecules to be detected to diffuse into the core of the active material of the sensor. Another drawback with sintering lies in the fact that it does not allow a sensor to be formed. The powders may be formed by processes consisting in incorporating the grains in an ink and then tracing the sensor using the techniques used in ink-jet printers. However, this technique gives films in which the grains are not connected on a macroscopic scale in relation to their size and it introduces solvents into the grains.

SUMMARY OF THE INVENTION

The object of the present invention is to provide a process for producing the sensitive element of a sensor for reducing molecules, comprising a tin oxide layer consisting of very fine grains having very good physical cohesion. This is why the subject of the present invention is a process for producing the sensitive element of such a sensor, and the sensor obtained.

The process according to the invention for producing the sensitive element of a sensor for reducing gas molecules is characterized in that:

during a first step, a layer of tin having a thickness of less than 1 μm, preferably less than 400 nm, is deposited electrochemically on the surface of an insulating support, by placing said insulating support in an electrochemical cell comprising an anode made of tin and a cathode which is a conductive film applied to the surface of the insulating support at one of its ends, the two electrodes being separated by an electrolyte consisting of a solution of a tin salt, and by passing a current of constant intensity through said cell;

during a second step, the tin layer obtained undergoes oxidation.

The intensity of the current is such that it creates a current density of between 1 $\mu A/cm^2$ and 5 $mA/cm^2$ in the plane perpendicular to the electrodes passing through the growth front of the film which is being deposited.

The concentration of the tin salt in the electrolyte is preferably between $10^{-3}$ mol/l and $10^{-1}$ mol/l.

DETAILED DESCRIPTION OF THE PREFERRED EMBODIMENTS

In one embodiment, the insulating support on which the layer has to be deposited constitutes one of the walls of the electrochemical cell. An insulating plate approximately of the same dimensions as said insulating support is parallel to said support and serves simply to close the cell, so as to protect it from air. The gap between the support and the insulating plate defines the electrolyte volume. The support and the plate may be kept apart by the metal contacts which allow the current to flow between the tin anode mounted inside the cell and the cathode formed by a conductive film deposited on that face of the support which is turned toward the interior of the cell at one of the ends of said face. The cathode may be a thin film of gold or of another metal. For example, if the metal forming the cathode is gold, a film of about 1000 Å is appropriate. To bring the cathode formed by a gold film into contact with the galvanostat that delivers the required current, it is possible to use metal blades or wires. In a flat cell as defined above, the thickness e of the tin layer obtained is determined simply by the formula $e = P \times h \times C/C_M$, in which h represents the distance between the two plates, that is to say the height of the electrolyte, C is the cation concentration of the electrolyte and $C_M$ is the molar concentration of the tin, that is to say the number of moles per liter of tin in the solid state. P is a parameter that can be related to the mobility of the cation and of the anion of the salt according to the formula $P=1+(\mu_c/\mu_a)$ $\mu_c$ and $\mu_a$ being the cation mobility and the anion mobility respectively. As a general rule, the cations and anions of a salt have very similar mobilities, and P is about 2. The simplified formula for determining e can therefore be written as: $e=2h\times C/C_M$.

At the start of the electrolysis step, the cathode serves to initiate the formation of the tin, which forms as a layer on the support. The tin layer deposited then remains adherent to the support.

The electrolyte may be an aqueous or nonaqueous solution of a tin salt. Aqueous solutions are preferred. The tin salt is preferably tin chloride or tin sulfate. The salt concentration in the electrolyte may vary very widely, depending on the quality and the compactness of the film that it is desired to obtain. A concentration of between 0.005 and 0.05 mol/l, more especially between 0.02 and 0.04 mol/l, is particularly preferred. It is preferred to use a tin salt solution kept away from air, so as to avoid the presence of hydroxides and carbonates.

Because the cell is operated at constant current, the growth rate of the tin layer is proportional to the intensity of the current, that is to say to the flux of atoms.

When it is desired to obtain a uniform tin layer, the electrochemical cell is subjected to a current having an intensity such that it creates a current density of between 0.05 and 5 mA/cm$^2$ in the plane perpendicular to the electrodes and passing through the growth front of the layer which is being deposited. In this case, when the electrolyte is a tin chloride solution prepared from a commercial tin chloride powder, layers consisting of grains having a mean size of around 300 nm are obtained. When an electrolyte is used that is obtained by diluting, to 0.01 mol/l, just before use, a very concentrated and highly acidic commercial tin chloride solution (for example solutions sold for sensitizing surfaces before silver plating in processes called electroless processes), the layer which is deposited on the support consists of disk-shaped wafers having a thickness of about 5 nm and a circumference of about 50 nm when the current density in the electrochemical cell is less than 1 mA/cm$^2$, this structure being determined by AFM (atomic force microscopy). Since the sensitivity to reducing atmospheres is dependent on screening phenomena between the adsorbed molecules and the active material of the sensor, it is the smallest dimension of the grains which determines the properties of the sensor. In the present case, the performance is therefore particularly good.

As a general rule, when it is desired to obtain a dendritic layer, the electrochemical cell is subjected to a current intensity of between 1 and 100 µA, preferably between 5 and 50 µA. At currents below about 1 µA, macrocrystals form which are of little interest for sensors. At currents above 100 µA, the metal is no longer deposited in the form of a layer on the support, but forms in the liquid. Electrolysis of the water may also occur instead of metal deposition. When the electrolyte is a highly acidic tin salt solution, it is necessary to impose a current density of greater than 20 µA to obtain a dendritic layer. In one particular embodiment, a support on one of the faces of which microscratches have been etched is used as support for depositing a dendritic tin layer. In this case, the dendrites of the layer which forms during the electrolysis follow the line of the microscratches. A polycrystalline microwire is thus obtained, the thickness and the cross section of which contain only a very small number of grains, or even a single grain, through the thickness. These grains have a size of less than or equal to 1 µm, generally around 100 to 300 nm.

The tin layer deposited on the support may be oxidized by air oxidation. It is advantageous to carry out a simultaneous heat treatment in order to accelerate the oxidation and the adsorption of oxygen at the grain boundaries. Oxidation and oxygen adsorption result in a significant increase in the resistance of the layer up to a plateau which depends on the thickness of the layer. When the layer is then subjected a reducing atmosphere, a significant drop in the resistivity is observed with a few seconds at room temperature. When the layer is returned to a normal atmosphere, the resistance resumes its initial value in few tens of seconds at room temperature.

The oxidation of the tin layer obtained during the first step of the process may be carried out after having constructed the sensor. In this case, when the tin layer has reached the desired length on the support during the first step, the electrochemical cell is opened, for example by removing the insulating plate that had served to close the cell on its upper part. The layer remains well adhered to the insulating support on which it was deposited. After having removed the electrolyte, two silver wires having a diameter of a few tens of a millimeter are bonded to the tin layer at its ends, the said silver wires being intended to serve as electrodes for the sensor. The assembly formed by the insulating support carrying the tin layer provided with silver wires is then subjected to an oxidizing atmosphere, for example the ambient atmosphere, optionally with a heat treatment.

The process for producing the tin oxide layer is particularly advantageous insofar as it produces very pure tin oxide in the form of a very thin layer directly on the support that will form part of the sensor. Furthermore, it allows working at room temperature, in a liquid medium, without the use of difficult techniques. By controlling the intensity of the current applied during the electrolysis, it is possible to define the thickness and the morphology of the layer deposited (homogeneous layer or dendritic layer). Furthermore, the fact that the current flows through the grains during deposition of the tin in metal form guarantees that the tin oxide grains obtained after oxidation of the tin layer will be physically connected. Surprisingly, the oxidation of the tin layer does not cause the grains to be disconnected to an extent which could modify the conductivity properties of the oxide layer used as sensitive element of a sensor.

In the processes of the prior art for preparing tin oxide, it is necessary to apply particular treatments, for example sintering treatments, or severe heat treatments such as calcining operations, in order to obtain a conductive material. Finally, because the sensitive element of the sensor of the present invention is produced in liquid medium, it is perfectly well suited to operating in such a medium.

According to the present invention, a sensitive element of a sensor for reducing gas molecules is formed by an insulating support coated with a tin oxide layer and is characterized in that the tin oxide layer is polycrystalline and has a thickness of less than 1 µm, preferably less than 400 nm.

In one particular embodiment, the tin oxide layer is substantially a single grain through the thickness, that is to say the grain size is substantially equivalent to the thickness of the oxide layer.

A sensor for reducing gas molecules may be formed by a sensitive element according to the invention connected to two electrodes, a controller and an ohmmeter or an impedance bridge.

In one particular embodiment, the tin oxide layer is a homogeneous layer.

In another embodiment, the tin oxide layer has a dendritic morphology. The grain boundaries are very accessible to the atmosphere. Furthermore, the tree structure of the grains can be likened to a wire structure. The presence of small grains along the path of the current, or along this wire, is sufficient to make the sensor very efficient. It has also been found that some of the grains have wasp waists which, without constituting two grain boundaries, remain preferential sites for detecting the change in conductivity associated with the presence of reducing molecules. The wire structure may be accentuated by using a support in which microscratches have been etched. This technique is easy and makes it possible to obtain alignments of grains of any shape, since the grains are deposited along the scratch, which may have a straight shape or any shape.

The present invention will be described in greater detail with reference to the examples given below.

Example 1

Preparation of an Oxide Layer

For the first step of the process, namely for preparing the tin film, an electrochemical cell was used consisting of a microscope slide (serving as support for the deposition) and a thin microscope slide, both having sides of 1.8 cm, kept 0.1 mm apart by two rectangular foils cut from a metal tin foil (sold by Goodfellow), one of the foils ensuring connection between the generator and the cathode, the other foil ensuring connection between the generator and the anode. The electrolyte was a 0.1 mol/l acidic aqueous tin chloride solution. The cathode consisted of a gold film 1000 Å in thickness, applied by evaporation at one of the ends of the internal face of the slide serving as support, the rest of this internal face having been presensitized by the evaporation of a layer of gold having a thickness of 20 Å, which does not conduct a current. The intensity of the current I delivered by the galvanostat was 30 μA.

The measurements taken showed that the grain sizes were typically between 200 and 600 nm.

The tin layer was then oxidized by heating at 100° C. for 4 hours in a chamber in which air was circulated.

Example 2

Detection Trials

A sensor comprising as sensitive element a dendritic layer having grains of around 400 nm was used to detect the carbon dioxide contained in cigarette smoke. The contacts between the support, formed by the microscope slide and coated with the tin oxide layer, and an ohmmeter were produced by the use of silver lacquer deposited on the layer and of silver wires.

Cigarette smoke was drawn into a glass chamber having a volume of 0.5 l, the chamber being kept sealed. When the temperature of the smoke reached room temperature, an opening was made in the chamber with a diameter of about 5 cm, and the sensor was advanced to within a few cm of the opening, and then moved away. The advancing and retreating operations were repeated several times, the resistivity of the sensor being measured continuously.

A response time of 2.5 seconds was found when the sensor was brought into contact with the smoke, whereas the tin oxide sensors of the prior art, called Taguchi sensors, have a response time of about 10 seconds to 1 min, depending on the type. When the sensor of the invention is moved away from the smoke, it recovers its normal resistivity in 30 seconds.

Comparative measurements were taken with a similar sensor, but not having a tin oxide film, the sensitive element being formed by the microscope slide carrying the silver lacquer and connected to the ohmmeter by silver wires. No change in the resistivity was observed when this comparative sensor was brought into contact with the smoke.

The invention claimed is:

1. A process for producing the sensitive element of a sensor for reducing gas molecules, characterized in that:
   during a first step, a layer of tin having a thickness of less than 1 μm is deposited electrochemically on the surface of an insulating support, by placing said insulating support in an electrochemical cell comprising an anode made of tin and a cathode which is a conductive film applied to the surface of the insulating support at one of its ends, the two electrodes being separated by an electrolyte consisting of a solution of a tin salt, and by passing a current of constant intensity through said cell;
   during a second step, the tin layer obtained undergoes oxidation.

2. The process as claimed in claim 1, characterized in that a current intensity is applied such that it creates a current density of between 1 $\mu A/cm^2$ and 5 $mA/cm^2$ in the plane perpendicular to the electrodes passing through the growth front of the layer which is being deposited.

3. The process as claimed in claim 2, characterized in that the current density is between 0.05 $mA/cm^2$ and 5 $mA/cm^2$.

4. The process as claimed in claim 3, characterized in that the current density is less than 1 $mA/cm^2$.

5. The process as claimed in claim 2, characterized in that the current density is between 1 $\mu A/cm^2$ and 100 $\mu A/cm^2$.

6. The process as claimed in claim 1, characterized in that the concentration of the tin salt in the electrolyte is between 10-3 mol/l and 10-1 mol/l.

7. The process as claimed in claim 6, characterized in that the concentration of the tin salt in the electrolyte is between 0.005 mol/l and 0.05 mol/l.

8. The process as claimed in claim 1, characterized in that:
   the insulating support on which the layer has to be deposited constitutes one of the walls of the electrochemical cell;
   an insulating plate approximately of the same dimensions as said insulating support is parallel to said support and serves to close the cell, the gap between the support and the insulating plate defining the electrolyte volume;
   the support and the plate are kept apart by metal contacts which allow the current to flow between the tin anode mounted inside the cell and the cathode formed by a conductive film deposited on that face of the support which is turned toward the interior of the cell and at one of the ends of said face.

9. The process as claimed in claim 1, characterized in that the cathode is a thin gold film having a thickness of about 1000 Å.

* * * * *